(12) United States Patent
Yamashita et al.

(10) Patent No.: US 10,159,766 B2
(45) Date of Patent: Dec. 25, 2018

(54) LAYERED CELL SHEET INCORPORATING HYDROGEL

(71) Applicant: iHeart Japan Corporation, Kyoto (JP)

(72) Inventors: Jun Yamashita, Kyoto (JP); Yasuhiko Tabata, Kyoto (JP); Takehiko Matsuo, Kyoto (JP)

(73) Assignee: IHEART JAPAN CORPORATION, Kyoto (JP)

( * ) Notice: Subject to any disclaimer, the term of this patent is extended or adjusted under 35 U.S.C. 154(b) by 0 days.

(21) Appl. No.: 14/894,610

(22) PCT Filed: May 30, 2014

(86) PCT No.: PCT/JP2014/064384
§ 371 (c)(1),
(2) Date: Nov. 30, 2015

(87) PCT Pub. No.: WO2014/192909
PCT Pub. Date: Dec. 4, 2014

(65) Prior Publication Data
US 2016/0121025 A1  May 5, 2016

(30) Foreign Application Priority Data
May 31, 2013 (JP) ................................. 2013-116388

(51) Int. Cl.
*A61L 27/52* (2006.01)
*C12N 5/077* (2010.01)
*A61L 27/36* (2006.01)

(52) U.S. Cl.
CPC ........... *A61L 27/52* (2013.01); *A61L 27/3604* (2013.01); *C12N 5/0657* (2013.01); *A61L 2430/20* (2013.01); *C12N 2513/00* (2013.01); *C12N 2533/54* (2013.01)

(58) Field of Classification Search
CPC .. A61L 27/3813; A61L 27/52; A61L 27/3839; A61L 2430/26; A61L 2430/20; A61L 27/3604; A61F 2/02; C12N 2513/00; C12N 2533/54; C12N 5/0657
USPC ................. 435/371, 325, 382; 424/93.7, 423
See application file for complete search history.

(56) References Cited

U.S. PATENT DOCUMENTS

| | | | |
|---|---|---|---|
| 2004/0235161 A1* | 11/2004 | Tabata | A61L 27/3813 435/371 |
| 2007/0207540 A1 | 9/2007 | Akashi et al. | |
| 2008/0226692 A1 | 9/2008 | Sato et al. | |
| 2011/0104122 A1 | 5/2011 | Yamashita et al. | |
| 2011/0151565 A1 | 6/2011 | Hase et al. | |
| 2011/0217726 A1* | 9/2011 | Matsusaki | G01N 33/5032 435/29 |
| 2012/0225483 A1 | 9/2012 | Tabata | |
| 2015/0032223 A1 | 1/2015 | Miyagawa et al. | |

FOREIGN PATENT DOCUMENTS

| | | |
|---|---|---|
| EP | 2 692 859 | 2/2014 |
| JP | 2007-228921 | 9/2007 |
| JP | 2011-130720 | 7/2011 |
| JP | 2011-224398 | 11/2011 |
| JP | 2012-120696 | 6/2012 |
| JP | 2013-198437 | 10/2013 |
| JP | 2014-75979 | 5/2014 |
| WO | 2008/143149 | 11/2008 |
| WO | 2009/118928 | 10/2009 |
| WO | 2011/059112 | 5/2011 |
| WO | 2012/133945 | 10/2012 |

OTHER PUBLICATIONS

SHimizu et al. vol. 24, Issue 13, Jun. 2003, pp. 2309-2316.*
Extended European Search Report dated Dec. 2, 2016 in European patent application No. 14 80 3665.
Takehiko Matsuo et al., "Abstract 11283: Efficiently Piled-Up Cardiac Tissue-Like Sheets With Pluripotent Stem Cell-Derived Cells Robustly Promotes Cell Engraftment and Ameliorates Cardiac Dysfunction After Myocardial Infarction", Circulation, vol. 128, Nov. 2013, p. A11283.
International Search Report dated Sep. 16, 2014 in International Application No. PCT/JP2014/064384.
Takehiko Matsuo et al., "Effectiveness of Gelatin Hydrogel Microspheres on Multilayer Formation in Cardiac Tissue Sheet", Regenerative Medicine, 2014, vol. 13, Suppl., p. 203, #O-12-6 and its English translation.
Tatsuya Shimizu et al., "Cell sheet engineering for myocardial tissue reconstruction", Biomaterials, 2003, vol. 24, pp. 2309-2316.
Ko Sugibayashi et al., "Preparation of Vascular-like Luminal Structure in Laminated Cell Sheet by Insertion of Biodegradable Hydrogel", Regenerative Medicine, 2010, vol. 9, Suppl., p. 176, #O-10-5 and its English translation.
Kentaro Hayashi et al., "Preparation of stem cell aggregates with gelatin microspheres to enhance biological functions", Acta Biomaterialia, 2011, vol. 7, pp. 2797-2803.
Hidetoshi Masumoto et al., "Pluripotent Stem Cell-Engineered Cell Sheets Reassembled with Defined Cardiovascular Populations Ameliorate Reduction in Infarct Heart Function Through Cardiomyocyte-Mediated Neovascularization", STEM Cells, 2012, vol. 30, No. 6, pp. 1196-1205.
Yuji Haraguchi et al., "Fabrication of functional three-dimensional tissues by stacking cells sheets in vitro", Nature Protocols, 2012, vol. 7, No. 5, pp. 850-858.
Tadashi Sasagawa et al., "Design of prevascularized three-dimensional cell-dense tissues using a cell sheet stacking manipulation technology", Biomaterials, 2010, vol. 31, pp. 1646-1654.

(Continued)

*Primary Examiner* — Janet L Epps-Smith
(74) *Attorney, Agent, or Firm* — Wenderoth, Lind & Ponack, L.L.P.

(57) ABSTRACT

The present invention relates to layered cell sheets comprising living cells and methods for producing the same. Specifically, the present invention provides methods for layering cell sheets, comprising layering cell sheets using hydrogel or preferably gelatin hydrogel. The present invention also provides layered cell sheets produced by such methods, and pharmaceutical compositions or therapeutic agents comprising layered cell sheets.

16 Claims, 5 Drawing Sheets

(56) References Cited

OTHER PUBLICATIONS

Jun Yamashita et al., "Flk1-positive cells derived from embryonic stem cells serve as vascular progenitors", Nature, 408:92-6, Nov. 2, 2000.

Jun K. Yamashita et al., "Prospective identification of cardiac progenitors by a novel single cell-based cardiomyocyte induction", The FASEB Journal, 19:1534-6, 2005.

* cited by examiner

FIG. 5 ial layers and, to that end, thicker sheets containing large
LAYERED CELL SHEET INCORPORATING HYDROGEL

TECHNICAL FIELD

The present invention relates to layered cell sheets incorporating hydrogel, preferably gelatin hydrogel, or more preferably gelatin hydrogel particles and a method for producing the same.

BACKGROUND ART

Cell transplantation therapies using cell sheets have been recently studied as medicine to supplement tissue deficient in cells due to disease or injury with cells. In particular, cardiomyocyte replacement therapy has been studied because adult cardiomyocytes rarely proliferate and, therefore, loss of cardiomyocytes caused by ischemic heart disease etc. becomes irreversible damage.

Accordingly, use of cardiomyocyte sheets produced from cardiomyocytes has been proposed. For such regenerative therapies to be successful, sufficient engraftment of the cardiovascular cell fraction is essential. Moreover, methods using, as cardiomyocytes for such a purpose, cardiac cell fractions derived from embryonic stem cells (ESC) or induced pluripotent stem cells (iPSC) (Non-patent documents 1 and 2 and Patent document 1) have been studied.

Reduction of cardiac function in rat after myocardial infarction was confirmed to be suppressed by transplanting 3 layers cardiac tissue sheets produced from these cells. However, this reduction was not caused by direct effects of the induced cardiomyocytes, but by suppression of left ventricle remodeling by indirect paracrine effects including angiogenesis due to cytokines released by the cells (Non-patent document 3).

Therefore, administration of more cardiomyocytes is necessary to have cardiomyocyte sheets engrafted onto myocardial layers and, to that end, thicker sheets containing large amounts of cardiomyocytes are desired. However, it has been confirmed that even upon transplantation of 4 or more layers of cardiomyocyte sheets without blood vessels, some cells do not survive due to the shortage of oxygen and nutrient supply and therefore the number of engrafted cells does not change. Accordingly, further technological development is considered to be necessary to produce effective cardiomyocyte sheets in cell replacement therapies.

Gelatin hydrogel is a biodegradable biomaterial that can be used as a cell culture substrate or scaffolding material and inclusion of particles of the gel in aggregates of cultured cells, for example, has been reported to improve oxygen supply, etc., and thus the condition of cells (Non-patent document 4 and Patent document 2).

Known methods of using gelatin hydrogel to produce cell sheets for transplant include a method of attaching gelatin hydrogel to sheets to make the cell sheets easy to be detached from the cell culture substrate (Patent documents 3, 4, and 5).

CITATION LIST

Patent Documents

Patent document 1: WO. 2009/118928
Patent document 2: WO. 2011/059112
Patent document 3: Japanese Unexamined Patent Application Publication No. 2011-224398
Patent document 4: Japanese Unexamined Patent Application Publication No. 2013-198437
Patent document 5: Japanese Unexamined Patent Application Publication No. 2014-75979

Non-Patent Documents

Non-patent document 1: Yamashita J, et al., Nature, 408:92-6, 2000
Non-patent document 2: Yamashita J K, et al., FASEB J. 19:1534-6, 2005
Non-patent document 3: Masumoto H, et al., Stem Cells, 30:1196-205, 2012
Non-patent document 4: Hayashi K, Tabata Y., Acta Biomater. 7:2797-803, 2011

SUMMARY OF INVENTION

Technical Problem

Purposes of the present invention relate to layered cell sheets incorporating hydrogel, preferably hydrogel particles, or more preferably gelatin hydrogel particles or to pharmaceutical compositions comprising the sheets and methods of layering cell sheets using hydrogel, preferably hydrogel particles, or more preferably gelatin hydrogel particles.

An object of the present invention is to layer cell sheets for preventing reduction of the number of living cells in cell sheets and reduction in cell function.

The present inventors found that the number of living cells in cell sheets significantly increases by layering the cell sheets using a specific type of hydrogel material, preferably gelatin hydrogel, or more preferably gelatin hydrogel particles, to attain the aforementioned object. Furthermore, it was confirmed that cells survive in 5 or more layers of sheets layered by this method and the sheets have improved functions.

Based on the results described above, the present inventors have succeeded in layering cell sheets using gelatin hydrogel particles and completed the present invention.

Accordingly, the present invention includes the following features:

[1] A method for layering cell sheets, comprising a step of layering cell sheets using hydrogel;
[2] The method according to [1], wherein the hydrogel is made of a material or in a form allowing diffusion of substances necessary for cell survival;
[3] The method according to [1] or [2], wherein the hydrogel is gelatin hydrogel;
[4] The method according to any of [1] to [3], wherein the hydrogel is hydrogel particles;
[5] The method according to [4], wherein the hydrogel gel particles are gelatin hydrogel particles;
[6] The method according to [5], wherein the gelatin hydrogel gel particles are gelatin hydrogel particles having intermolecular cross-linking between gelatin molecules;
[7] The method according to [5] or [6], wherein the gelatin hydrogel particles consist of particles having particle sizes of 20 μm to 32 μm in a dry state;
[8] The method according to any of [1] to [7], comprising a step of adding the hydrogel, preferably the hydrogel particles, or more preferably the gelatin hydrogel particles between a first cell sheet or first layered cell sheets and a second cell sheet or second layered cell sheets;
[9] The method according to [8], wherein the layered cell sheets consist of 2 or 3 cell sheets;

[10] The method according to [8] or [9], comprising a step of adding the hydrogel, preferably the hydrogel particles, or more preferably the gelatin hydrogel particles at an amount of 500 µg/cm² to 2000 µg/cm² unit area of cell sheet;

[11] Layered cell sheets layered by the method according to any of [1] to [10];

[12] The layered cell sheets according to [11], comprising 4 or more cell sheets being layered;

[13] A pharmaceutical composition comprising the layered cell sheets according to [11] or [12];

[14] The method according to any of [1] to [10], wherein the cell sheets are cardiomyocyte sheets;

[15] The method according to any of [1] to [10], wherein the cell sheets are cardiac cell sheets comprising cardiomyocytes, endothelial cells, and mural cells;

[16] The method according to [14] or [15], wherein the cardiomyocytes are produced from a pluripotent stem cell;

[17] The method according to [15] or [16], wherein the endothelial cells are produced from a pluripotent stem cell;

[18] The method according to any of [15] to [17], wherein the mural cells are produced from a pluripotent stem cell;

[19] The method according to any of [14] to [18], wherein the pluripotent stem cell is an induced pluripotent stem cell (iPS cell);

[20] Layered cell sheets layered by the method according to any of [14] to [19];

[21] The layered cell sheets according to [20], comprising 4 or more cell sheets being layered;

[22] A therapeutic agent for cardiac diseases, comprising the layered cell sheets according to any of [11], [12], [20], and [21].

Advantageous Effects of Invention

The methods according to the present invention make it possible to layer cell sheets with cells alive. Moreover, the resultant cell sheets can be used for application to cell replacement therapies.

BRIEF DESCRIPTION OF DRAWINGS

FIG. 3 illustrates photographs of tissue preparations and quantification results of layered sheets (5 layers) according to the present invention. Panel A illustrates hematoxylin eosin (HE) staining images from a subject group (control) which were layered without using gelatin hydrogels, a group (low dose) in which 250 µg of gelatin hydrogel fine particles (with particle sizes of 20-32 µm in a dry state) were added to each layer, and a group (high dose group) in which 750 µg of gelatin hydrogel fine particles (with particle sizes of 20-32 µm in a dry state) were added dropwise. In the figure, the black arrow heads indicate gelatin hydrogel fine particles. In panel B, the left graph illustrates the comparison of the thicknesses of cell sheets between the groups and the right graph illustrates the comparison of the areas of HE staining-positive cell regions between the groups.

FIG. 4 illustrates photographs of tissue preparations and quantification results of layered sheets (5 layers) according to the present invention. Panel A illustrates hematoxylin eosin (HE) staining images of a subject group (control) layered without using gelatin hydrogel, a group in which particles having particle sizes of less than 20 µm in a dry state were added dropwise, a group in which particles having particle sizes of 20-32 µm in a dry state were added dropwise, and a group in which particles having particle sizes of 32-53 µm in a dry state were added dropwise. In panel B, the left graph illustrates the comparison of thicknesses of cell sheets between the groups and the right graph illustrates the comparison of the areas of HE staining-positive cell regions between the groups.

DESCRIPTION OF EMBODIMENTS

1. Hydrogel

As used herein, "hydrogel" refers to a substance which is capable of containing water in large quantities, made of a material or in a form readily allowing diffusion of substances necessary for cell survival such as oxygen, water, water-soluble nutrients, and polypeptides such as enzymes and cytokines, wastes, and the like, and usually biocompatible. The shape and form of the hydrogel are not particularly limited, as long as it can be incorporated in the cell sheets, but various shapes and forms such as, for example, particulate, granular, film, tubular, disk, reticulate, mesh, porous, suspension, or dispersion shapes or forms can be used. In particular, hydrogel particles that are formed as a result of solidification of an aqueous solution containing colloidal particles are preferred. Particles made of any material can be used as long as they have the aforementioned properties of hydrogel. Examples include particles made of hydrogel of cross-linked water-soluble, hydrophilic, or water absorptive synthetic polymers such as polyacrylamide, polyacrylic acid, polyhydroxyethyl methacrylate, polyvinyl alcohol, polylactic acid, and polyglycolic acid; and polysaccharide, protein, and nucleic acid. Examples of polysaccharide include, but are not limited to, glycosaminoglycan such as hyaluronic acid and chondroitin sulfate, starch, glycogen, agarose, pectin, cellulose, etc. Examples of protein include, but are not limited to, collagen and its hydrolysate gelatin, proteoglycan, fibronectin, vitronectin, laminin, entactin, tenascin, thrombospondin, von Willebrand factor, osteopontin, fibrinogen, etc. Particles suitable for the present invention are preferably those that are biocompatible and made of materials that are degraded by cells in the body, and more preferably particles made of gelatin. Therefore, in the present invention, preferred hydrogel gel particles are gelatin hydrogel particles.

In the present invention, hydrogel or hydrogel particles obtained by coating the surface of the aforementioned hydrogel, preferably the hydrogel particles, or more preferably the gelatin hydrogel particles with a cell-adhesive protein such as collagen, fibronectin, vitronectin, laminin, glycosaminoglycan, etc. and active peptides thereof, or a biologically functional sugar, oligosaccharide, polysaccharide, or the like or by immobilizing such a substance onto the surface can be used to improve culture conditions and the proliferation of cells.

The gelatin hydrogel particles used in the present invention are microparticulate gelatin hydrogel which is obtained by cross-linking gelatin molecules by subjecting the gelatin molecules to a chemical reaction, thermal dehydration process, radiation, ultraviolet radiation, or electron beam irradiation. As a chemical cross-linker, water-soluble carbodiimide such as EDC, propylene oxide, a diepoxy compound, and a condensing agent which forms a chemical bond between two of hydroxyl, carboxyl, amino, thiol, imidazole groups, and the like can be used.

The gelatin in the present invention refers to denatured collagen, in which salt bonds and hydrogen bonds between peptide chains of collagen have been cleaved by acid or alkali or enzymatic treatment etc. so that the collagen changes irreversibly into a water-soluble protein. The collagen may be collected from an animal or a plant or a recombinant collagen may be used. The gelatin used in the present invention may be either of acid gelatin and basic gelatin. As used herein, "acid gelatin" encompasses gelatin which is prepared by treating collagen with alkali and has an isoelectric point equal to or more than 2.0 and less than 7.0, preferably equal to or more than about 4.0 and equal to or less than about 6.5, more preferably equal to or more than about 4.5 and equal to or less than about 5.5. "Basic gelatin" encompasses gelatin which is prepared by treating collagen with acid and has an isoelectric point equal to or more than about 7.0 and equal to or less than about 13.0, preferably equal to or more than about 7.5 and equal to or less than about 10.0, or more preferably equal to or more than about 8.5 and equal to or less than about 9.5. For example, as "acid gelatin," the sample with isoelectric point (IEP) of about 5.0 from Nitta Gelatin Inc. or the like can be used, and as basic gelatin, similarly, the sample with IEP 9.0 from Nitta Gelatin Inc. or the like can be used. More preferably, the gelatin is "acid gelatin" having an isoelectric point of about 5.0.

The degree of cross-linking of gelatin can be selected as appropriate depending on the desired water content, that is, the level of bioabsorbability of the hydrogel. In the preparation of gelatin hydrogel, the preferred ranges of concentrations of gelatin and cross-linker are about 1 to about 20 w/w % for the gelatin concentration and about 0.01 to about 1 w/w % for the cross-linker concentration. The cross-linking conditions are not particularly limited, but the cross-linking can be carried out, for example, at about 0 to about 160° C., for about 1 to about 48 hours. Generally, increase of the concentrations of gelatin and cross-linker and the cross-linking time increases the cross-linking degree of the hydrogel and decreases the bioabsorbability of the gelatin hydrogel. Alternatively, the gelatin can be cross-linked by thermal dehydration at high temperature under reduced pressure. The thermal dehydration cross-linking can be carried out, for example, at about 80 to about 160° C. or preferably about 120 to about 140° C. under reduced pressure of around 0.1 Torr for about 1 to about 48 hours. The degree of swelling of hydrogel particles varies depending on the cross-linking degree. When using hydrogel particles in layered cell sheets, they are available without necessity of particularly limiting the degree of cross-linking of the hydrogel. The cross-linking degree can be expressed, for example, by the water content (weight of hydrogel in swollen state/weight of hydrogel in dry state×100). The water content of the hydrogel particles used in the present invention is not particularly limited, but it is about 85 to about 99%.

The gelatin hydrogel particles can be produced by a known method. For example, the gelatin hydrogel particles can be prepared, as one method, by placing a gelatin solution in an apparatus that has a fixed stirring motor (for example, Three one motor supplied by Shinto Scientific Co., Ltd., EYELA mini D.C. stirrer, or the like) and a propeller for Teflon (registered trademark) mounted to a three neck round bottom flask and are fixed together with the flask; adding thereto an oil such as an olive oil and stirring at a speed of around about 200 to about 600 rpm to form a W/O emulsion; and adding thereto an aqueous solution of a cross-linker to form cross-linking between gelatin molecules. Alternatively, after the W/O emulsion is cooled, acetone, ethyl acetate, or the like is added thereto and stirred, and uncross-linked gelatin particles are collected by centrifugation. The collected gelatin particles are washed further with acetone, ethyl acetate, or the like and then with 2-propanol, ethanol, or the like and then dried. The dried gelatin particles can be sieved at this stage to obtain particles of required sizes, as appropriate, depending on the purpose. The gelatin hydrogel particles can be produced by cross-linking those dried gelatin particles. In addition, the gelatin hydrogel particles may be produced by adding dropwise into an olive oil an emulsion obtained by a pre-emulsification of a gelatin aqueous solution in an olive oil (for example, using the vortex mixer Advantec TME-21, a homogenizer, Polytron PT10-35, or the like) to prepare a microparticulate W/O emulsion; and adding thereto an aqueous solution of a cross-linker to cause cross-linking reaction. The thus obtained gelatin hydrogel particles are collected by centrifugation, then washed with acetone, ethyl acetate, or the like, and further immersed in 2-propanol, ethanol, or the like to stop the cross-linking. The obtained gelatin hydrogel particles are washed with 2-propanol, distilled water containing Tween 80, and distilled water, in this order, and then used for cell culturing. When gelatin hydrogel particles aggregate, for example, a surfactant or the like may be added or sonication (preferably with cooling and within around 1 minute) may be employed.

The average particle diameter of the obtained gelatin hydrogel particles varies depending on the gelatin concentration at the time of the aforementioned particle production, the volume ratio of the gelatin aqueous solution and the olive oil, the stirring speed, and the like. In general, the particle diameters are about 500 nm to about 1000 μm and particles of required sizes may be obtained by sieving as appropriate depending on the purpose. As used herein, "particle diameter" may be referred to as "particle size." "Particle diameter," "particle size," and "particulate diameter" are used interchangeably. Furthermore, microparticulate gelatin hydrogel particles having particle sizes of about 50 nm to about 20 μm or less can be obtained by conducting the preemulsification. Furthermore, particles having sizes of about 50 nm to about 1 μm can be obtained by causing phase separation of gelatin in the aqueous solution state to make it self-assemble. The phase separation is accomplished by known techniques including addition of a second component, changing pH, ionic strength, or the like of the aqueous solution.

In the present invention, preferred particle sizes obtained by sieving are about 50 nm to about 1000 µm, about 500 nm to about 1000 µm, more preferably about 1 µm to about 200 µm, further more preferably about 10 to about 50 µm, and 20 to 32 µm. Here, the particle size is preferably expressed by the particle size in a dry state because the particle may swell in a solvent.

In addition, the gelatin hydrogel particles may be produced by, for example but not limited to, the method described in WO 2011/059112.

Hydrogel particles other than gelatin hydrogel particles can be also produced from hydrogel by a similar or known technique. Moreover, the most suitable range of particle diameters can be determined by measuring the living cell region area and the thickness of layered cell sheets by a method described in Example 1 after producing layered cell sheets using a variety of particle diameters of hydrogel particles.

2. Cells to be Used to Produce Cell Sheets

Cells to produce cell sheets are, but not limited to, cells of mammals, including humans, and, for example, somatic cells, precursor cells thereof, or mixed cells thereof.

In the present invention, cell sheet is a sheet-like cell aggregate in which cells are connected by cell junction. The type of cells is not particularly limited, but the cells are cells of mammals including humans, and, for example, somatic cells, precursor cells thereof, or mixed cells thereof. Specifically, examples of the cells include, but not limited to, cardiomyocytes, endothelial cells (for example, vascular endothelial cells and lymphatic endothelial cells), mural cells (for example, pericytes), muscle cells (for example, skeletal muscle cells and smooth muscle cells), epithelial cells (for example, epidermal cells, dermal cells, gastrointestinal epithelial cells, respiratory tract epithelial cells, esophageal epithelial cells, renal pelvis epithelial cells, ureter epithelial cells, bladder epithelial cells, urethra epithelial cells, and prostatic ductal cells), chondrocytes, periodontal ligament cells, neural cells (for example, nerve cells and glial cells), hair papilla cells, bone cells, precursor cells thereof, and mixed cells thereof. These cells may be cells contained in a tissue isolated by any method, or may be from a cell strain established from a tissue. In addition, the cells may be cells induced from pluripotent stem cells by any method. The method of induction to be used for the purpose is not particularly limited and a method well known for those skilled in the art can be used, but examples include a method of forming an embrycid body described in Japanese Unexamined Patent Application Publication No. 2003-523766.

Moreover, it is possible to layer cell sheets composed of a mixture of these cells or different types of cell sheets.

Cells to be used to produce cardiac cell sheets will be described below.

2.1. Method for Producing Cardiomyocyte, Endothelial Cell, and Mural Cell from Induced Pluripotent Stem Cells As used herein, "cardiomyocyte" refers to a cell expressing at least cardiac troponin (cTnT) or αMHC. An example of human cTnT is NCBI accession number NM_000364 and an example of mouse cTnT is NM_001130174. An example of human αMHC is NCBI accession number NM_002471 and an example of mouse αMHC is NM_001164171.

As used herein, "endothelial cell" refers to a cell expressing one of PE-CAM, VE-cadherin, and the von Willebrand factor (vWF). A mural cell refers to a cell expressing smooth muscle actin (SMA). An example of human PE-CAM is NCBI accession number NM_000442 and an example of mouse PE-CAM is NM_001032378. An example of human VE-cadherin is NCBI accession number NM_001795 and an example of mouse VE-cadherin is NM_009868. An example of human vWF is NCBI accession number NM_000552 and an example of mouse vWF is NM_011708. An example of human SMA is NCBI accession number NM_001141945 and an example of mouse SMA is NM_007392.

The pluripotent stem cells which can be used in the present invention are stem cells having both the pluripotency to differentiate into all types of cells in the body and an ability to proliferate. The pluripotent stem cells are not particularly limited, but include, for example, embryonic stem (ES) cells, embryonic stem (ntES) cells derived from a clonal embryo obtained by nuclear transplant, spermatogonial stem cells ("GS cells"), embryonic germ cell ("EG cells"), induced pluripotent stem (iPS) cells, and pluripotent cells derived from cultured fibroblasts or bone marrow stem cells (Muse cells). Preferred pluripotent stem cells are induced pluripotent stem cells ("iPS cells") from the viewpoint that they can be obtained without destroying an embryo, an ovum, or the like in the production process.

iPS cells can be produced by introducing reprogramming factors into any somatic cells. Examples of the reprogramming factors include genes or gene products such as Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, or Glis1. These reprogramming factors may be used alone or in combination. Examples of the combinations of reprogramming factors include combinations described in WO 2007/069666, WO 2008/118820, WO 2009/007852, WO 2009/032194, WO 2009/058413, WO 2009/057831, WO 2009/075119, WO 2009/079007, WO 2009/091659, WO 2009/101084, WO 2009/101407, WO 2009/102983, WO 2009/114949, WO 2009/117439, WO 2009/126250, WO 2009/126251, WO 2009/126655, WO 2009/157593, WO 2010/009015, WO 2010/033906, WO 2010/033920, WO 2010/042800, WO 2010/050626, WO 2010/056831, WO 2010/068955, WO 2010/098419, WO 2010/102267, WO 2010/111409, WO. 2010/111422, WO 2010/115050, WO 2010/124290, WO 2010/147395, WO 2010/147612, Huangfu D, et al. (2008), Nat. Biotechnol., 26: 795-797, Shi Y, et al. (2008), Cell Stem Cell, 2: 525-528, Eminli S, et al. (2008), Stem Cells, 26:2467-2474, Huangfu D, et al. (2008), Nat Biotechnol. 26:1269-1275, Shi Y, et al. (2008), Cell Stem Cell, 3, 568-574, Zhao Y, et al. (2008), Cell Stem Cell, 3:475-479, Marson A (2008), Cell Stem Cell, 3, 132-135, Feng B, et al. (2009), Nat Cell Biol. 11:197-203, R. L. Judson et al. (2009), Nat. Biotech., 27:459-461, Lyssiotis C A, et al. (2009), Proc Natl Acad Sci USA. 106:8912-8917, Kim J B, et al. (2009), Nature, 461:649-643, Ichida J K, et al. (2009), Cell Stem Cell, 5:491-503, Heng J C, et al. (2010), Cell Stem Cell, 6:167-74, Han J, et al. (2010), Nature, 463:1096-100, Mali P, et al. (2010), Stem Cells, 28:713-720, Maekawa M, et al. (2011), Nature, 474:225-9.

Somatic cells include, but not limited to, somatic cells of fetuses, somatic cells of newborn babies, and matured healthy or diseased somatic cells, as well as any of primary culture cells, subcultured cells, and established cells. Specifically, examples of somatic cells include, for example, (1) tissue stem cells (somatic stem cells) such as neural stem cells, hematopoietic stem cells, mesenchymal stem cells, and dental pulp stem cells, (2) tissue precursor cells, (3) differentiated cells such as lymphocytes, epithelial cells, endothelial cells, muscle cells, fibroblasts (skin cells), hair cells, hepatocytes, gastric mucosa cells, enterocytes, splenocytes, pancreatic cells (pancreatic exocrine cells, etc.), brain cells, pneumocytes, kidney cells, and fat cells.

When iPS cells are used as a material of cells for transplantation, it is desired to use somatic cells having an HLA genotype identical or substantially identical to that of the recipient individual of the transplant from the viewpoint of preventing rejection. "Substantially identical" refers to having matches in the HLA genotype sufficient to suppress immune responses to transplanted cells by immunosuppressive agents. For example, somatic cells having an HLA type that has matches at 3 loci of HLA-A, HLA-B, and HLA-DR or at 4 loci including the 3 loci and HLA-C are substantially identical.

By the following steps (a) and (b), cardiomyocytes, endothelial cells, and mural cells can be simultaneously produced from an induced pluripotent stem cells ("iPS cells"):
(a) the step of producing cardiomyocytes from induced pluripotent stem cells,
(b) the step of culturing the cardiomyocytes obtained in step (a) in the presence of vascular endothelial cell growth factor (VEGF).

Moreover, cardiomyocytes, endothelial cells, and mural cells can be similarly produced from a stem cell such as an embryonic-stem cell ("ES cell") instead of the induced pluripotent stem cells, though concrete explanations are not provided here.

As a method for producing cardiomyocytes from induced pluripotent stem cells, for example, cardiomyocytes can be produced from pluripotent stem cells reported by Laflamme M A (Laflamme M A & Murry C E, Nature 2011, Review). In addition, examples include, but not limited to, a method for producing cardiomyocytes in which induced pluripotent stem cells are cultured in suspension to form a cell mass (embryoid body), a method for producing cardiomyocytes in the presence of a substance suppressing BMP signaling (WO 2005/033298), a method for producing cardiomyocytes by adding activin A and BMP sequentially (WO 2007/002136), a method for producing cardiomyocytes in the presence of a substance promoting the activation of the canonical Wnt signaling pathway (WO 2007/126077), and a method of producing cardiomyocytes in the presence of cyclosporin A, including isolating Flk/KDR-positive cells from induced pluripotent stem cells (WO 2009/118928).

In consideration of the safety of cell sheets to be used in the present invention, the method may further comprise the step of removing undifferentiated cells from mixed cells containing cardiomyocytes, endothelial cells, and mural cells produced by the aforementioned steps.

2.2. Method for Producing Mixed Cells Containing Cardiomyocytes from Induced Pluripotent Stem Cells Another preferred method for producing cardiomyocytes will be explained below.

This method includes the steps of:
(i) culturing induced pluripotent stem cells in a medium containing activin A; and
(ii) following to the step (i), further culturing the cells in a medium containing BMP4 and bFGF.

<Step of Culturing Cell in a Medium Containing Activin A>

In this step, an induced pluripotent stem cell is produced by a known method, separated, and cultured by a method, such as suspension culture and adherent culture using a culture dish treated by coating, preferably adherent culture.

A method of the separation may be mechanical or the use of a separation solution having a protease activity and a collagenase activity (including, for example, Accutase (trademark) and Accumax (trademark)) or a separation solution having only a collagenase activity. A method of dissociating cells using a separation solution having only a collagenase activity and mechanically separating them into smaller clusters is preferred. Preferably, the induced pluripotent stem cells to be used are from a colony cultured until 80% confluent in the dish being used.

The suspension culture refers to culturing cells in a state where cells are not adhered to the culture dish and can be performed, but not limited to, by using a dish not artificially treated (for example, coated with an extracellular matrix or the like) for the purpose of improving the adhesion to cells or a dish artificially treated (for example, coated with poly(hydroxyethyl methacrylate) (poly-HEMA)) for suppressing adhesion.

For adherent culture, cells are cultured in any medium in a coated culture dish. Examples of coating agents include Matrigel (BD), collagen, gelatin, laminin, heparan sulfate proteoglycan, or entactin and combinations thereof. Matrigel is preferred. More preferred is adherent culture by the Matrigel sandwich method in which induced pluripotent stem cells adhere to a culture dish coated with Matrigel and Matrigel is further added thereon to coat whole induced pluripotent stem cells with Matrigel.

The medium in this step can be prepared by using as a basal medium a medium to be used for culturing animal cells. Examples of the basal medium include IMDM medium, Medium 199, Eagle's Minimum Essential Medium (EMEM), αMEM, Doulbecco's modified Eagle's Medium (DMEM), Ham's F12 medium, 1640 RPMI medium, Fischer's medium, and mixed media thereof. 1640 RPMI medium is preferred. The medium may contain serum or may be serum free. For example, one or more serum substitutes such as albumin, transferrin, Knockout Serum Replacement (KSR) (a serum substitute of FBS for culturing ES cells), N2 supplement (Invitrogen), B27 supplement (invitrogen), fatty acids, insulin, collagen precursors, trace elements, 2-mercaptoethanol, and 3'-thiolglycerolmay, as well as one or more substances such as lipids, amino acids, L-glutamine, Glutamax (Invitrogen), non-essential amino acids, vitamins, growth factors, antibiotics, antioxidants, pyruvic acid, buffers, and inorganic salts can be contained as needed. Preferred growth factors include Wnt1, Wnt3, Wnt3a, Wnt4, Wnt7a, TGF-β, activin A, Nodal, BMP2, BMP4, BMP6, BMP7, GDF, bFGF, and VEGF. In this step, at least activin A (for example, (recombinant) human activin A) is preferably used as a growth factor.

Examples of preferred media include RPMI medium containing L-glutamine, B27 supplement, and Activin A.

The concentration of activin A added into the medium is, for example, but not limited to, 10 ng/mL, 25 ng/mL, 50 ng/mL, 60 ng/mL, 70 ng/mL, 80 ng/mL, 90 ng/mL, 100 ng/mL, 110 ng/mL, 120 ng/mL, 130 ng/mL, 140 ng/mL, 150 ng/mL, 175 ng/mL, or 200 ng/mL. Preferably, the concentration of activin A added into the medium is 100 ng/mL.

The culturing temperature is, but not limited to, about 30-40° C., preferably about 37° C. and the culturing is carried out in the atmosphere of $CO_2$-containing air with preferred $CO_2$ concentrations being about 2-5%. The culturing time is, for example, 1 to 5 days, and preferably 1 day.

<Step of Culturing Cells in a Medium Containing BMP and bFGF>

In this step, when the preceding step is performed in suspension culture, the obtained cell population may be cultured, as it is, in any medium in a coated culture dish. Examples of coating agents include Matrigel (BD), collagen, gelatin, laminin, heparan sulfate proteoglycan, or entactin and combinations thereof. Matrigel is preferred. Alternatively, when the preceding step is performed in adherent culture, cells may be continually cultured with medium changes.

The medium to be used in this step can be prepared by using as a basal medium a medium used for culturing animal cells. Examples of the basal medium include IMDM medium, Medium 199, Eagle's Minimum Essential Medium (EMEM), αMEM, Doulbecco's modified Eagle's Medium (DMEM), Ham's F12 medium, 1640 RPMI medium, Fischer's medium, and mixed media thereof. 1640 RPMI medium is preferred. Preferably, the medium is serum free. For example, one or more serum substitutes such as albumin, transferrin, sodium selenite, ITS-X (Invitrogen) (containing insulin, transferrin, and sodium selenite), Knockout Serum Replacement (KSR; a serum substitute of FBS for culturing ES cells), N2 supplement (Invitrogen), B27 supplement (Invitrogen), fatty acids, insulin, collagen precursors, trace elements, 2-mercaptoethanol, and 3'-thiolglycerol, as well as one or more substances such as lipids, amino acids, L-glutamine, Glutamax, non-essential amino acids, vitamins, growth factors, antibiotics, antioxidants, pyruvic acid, buffers, and inorganic salts can be contained as needed. Preferred growth factors in the present invention include Wnt1, Wnt3, Wnt3a, Wnt4, Wnt7a, TGF-β, activin A, Nodal, BMP2, BMP4, BMP6, BMP7, GDF, bFGF, and VEGF. In this step, at least BMP4 (for example, (recombinant) human BMP4) and bFGF (for example, (recombinant) human bFGF) are preferably used as growth factors.

Examples of preferred media in this step include RPMI medium containing L-glutamine, B27 supplement, BMP4, and bFGF.

The concentration of BMP4 added into the medium is, for example, but not limited to, 0.1 ng/mL, 0.5 ng/mL, 1 ng/mL, 2.5 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 ng/mL, 15 ng/mL, 17.5 ng/mL, 20 ng/mL, 30 ng/mL, 40 ng/mL, or 50 ng/mL. Preferably, the concentration of BMP4 added into the medium is 10 ng/mL.

The concentration of bFGF added into the medium is, for example, but not limited to, 0.1 ng/mL, 0.5 ng/mL, 1 ng/mL, 2.5 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 ng/mL, 15 ng/mL, 17.5 ng/mL, 20 ng/mL, 30 ng/mL, 40 ng/mL, or 50 ng/mL. Preferably, the concentration of bFGF added into the medium is 10 ng/mL.

The culturing temperature is, but not limited to, about 30-40° C., preferably about 37° C. and the culturing is carried out in the atmosphere of $CO_2$-containing air with preferred $CO_2$ concentrations being about 2-5%. The culturing time is, for example, 1 to 10 days, and preferably 4 days.

<Method for Culturing Cardiomyocytes in the Presence of VEGF>

In this step, mixed cells of cardiomyocytes, endothelial cells, and mural cells at desired composition ratios can be produced by culturing the cardiomyocytes obtained by the method described above in the presence of VEGF.

For example, the obtained cardiomyocytes in the cell population after the suspension culture in the preceding step may be cultured in any medium in a coated culture dish. Examples of coating agents include Matrigel (BD), collagen, gelatin, laminin, heparan sulfate proteoglycan, or entactin and combinations thereof. Matrigel is preferred. Alternatively, in this step, the cells obtained by adherent culture in the aforementioned step may be continually cultured by medium changes.

The medium to be used in this step can be prepared by using as a basal medium a medium used for culturing animal cells. Examples of the basal medium include IMDM medium, Medium 199, Eagle's Minimum Essential Medium (EMEM), αMEM, Dulbecco's modified Eagle's Medium (DMEM), Ham's F12 medium, 1640 RPMI medium, Fischer's medium, and mixed media thereof. 1640 RPMI medium is preferred. Preferably, the medium is serum free. For example, one or more serum substitutes such as albumin, transferrin, sodium selenite, ITS-X (Invitrogen; containing insulin, transferrin, and sodium selenite), Knockout Serum Replacement (KSR; a serum substitute of FBS for culturing ES cells), N2 supplement (Invitrogen), B27 supplement (Invitrogen), fatty acids, insulin, collagen precursors, trace elements, 2-mercaptoethanol, and 3'-thiolglycerol, as well as one or more substances such as lipids, amino acids, L-glutamine, Glutamax, non-essential amino acids, vitamins, growth factors, low molecular weight compounds, antibiotics, antioxidants, pyruvic acid, buffers, and inorganic salts can be contained as needed. Preferred growth factors include Wnt1, Wnt3, Wnt3a, Wnt4, Wnt7a, TGF-β, activin A, Nodal, BMP2, BMP4, BMP6, BMP7, GDF, bFGF, and VEGF. In this step, at least VEGF is preferably used as a growth factor.

Examples of preferred media include RPMI 1640 medium containing L-glutamine, B27 supplement, and VEGF.

For example, the concentration of VEGF added into the medium can be in the range of 10 ng/mL to 500 ng/mL, 25 ng/mL to 300 ng/mL, 40 ng/mL to 200 ng/mL, 50 ng/mL to 100 ng/mL, 60 ng/mL to 90 ng/mL, or 65 ng/mL to 85 ng/mL. Preferably, the concentration of VEGF added into the medium is 50 ng/mL to 100 ng/mL. Moreover, the concentration of VEGF added into the medium may be, but not limited to, 10 ng/mL, 25 ng/mL, 50 ng/mL, 55 ng/mL, 60 ng/mL, 65 ng/mL, 70 ng/mL, 75 ng/mL, 80 ng/mL, 85 ng/mL, 90 ng/mL, 95 ng/mL, 100 ng/mL, 110 ng/mL, 120 ng/mL, 130 ng/mL, 140 ng/mL, 150 ng/mL, or 200 ng/mL. Preferably, the concentration of VEGF added into the medium is 75 ng/mL.

The culturing temperature is, but not limited to, about 30-40'C, preferably about 37° C. and the culturing is carried out in the atmosphere of $CO_2$-containing air with preferred $CO_2$ concentrations being about 2-5%. The culturing time is, for example, 4 to 20 days (for example, 5 to 15 days), and preferably 10 days.

The cell composition ratios of cardiomyocytes, endothelial cells, and mural cells produced by the method described above per total cell number as measured by FACS analysis are, but not limited to, 40-80% of cardiomyocytes, 1-20% of endothelial cells, 1-45% of mural cells, and 0.1-10% of undifferentiated cells. Preferably, endothelial cells are contained at least around 3-12%. Examples of composition ratios of cardiomyocytes, endothelial cells, and mural cells include mixed cells of a composition ratio of 62.7% of cardiomyocytes, 7.9% of endothelial cells, 18.3% of mural cells, and 2.7% of undifferentiated cells, or mixed cells of a composition ratio of 45.6±3.8% of cardiomyocytes, 9.9±1.7% of endothelial cells, and 41.8±3.3% mural cells. The cell composition ratio of cardiomyocytes, endothelial cells, and mural cells according to the present invention can be arbitrarily changed based on the concentration of VEGF and various other culture conditions, and can be arbitrarily changed within the range to keep appropriate strength when cells are formed into a sheet.

<Step of Removing Undifferentiated Cells (TRA-1-60-positive Cells)>

Furthermore, it is preferred to remove undifferentiated cells from the mixed cells of cardiomyocytes, endothelial, and mural cells produced in the above step.

This step can adopt any method that can separate undifferentiated cells from cardiomyocytes, endothelial cells, and mural cells in the mixed cells. The separation of undifferentiated cells from the mixture of cardiomyocytes, endothelial cells, and mural cells may be a method of removing only undifferentiated cells from the mixed cells based on an index of undifferentiated cells, or may be a method of removing cardiomyocytes, endothelial cells, and mural cells from mixed cells based on indices of cardiomyocytes, endothelial cells, and mural cells. Preferably, the former method is used in this step.

Indices of undifferentiated cells can be, for example, genes or proteins specifically expressed in undifferentiated cells. These genes or proteins are sufficiently known in the art (Cell., 2005 Sep. 23, 122 (6):947-56, Stem Cells, 2004, 22(1):51-64, Mol Biol Cell, 2002 April; 13(4):1274-81), and examples include, but not limited to, Oct3/4, Nanog (the foregoing are transcription factors), SSEA-3, SSEA-4, TRA-1-60, TRA-1-81 (the foregoing are cell surface antigens). The index used in this step is preferably a cell surface antigen and particularly preferably TRA-1-60 is used as an index.

The indices of cardiomyocytes, endothelial cells, and mural cells are, for example, but not limited to, cardiac troponin-T (cTnT) (cardiomyocyte), VE-cadherin (endothelial cell), and PDGFRb (mural cell), respectively.

The removal of undifferentiated cells in this step is carried out based on an index mentioned above using, for example, a method such as flow cytometry (FACS), magnetic cell separation method (MACS), etc. MACS is preferred.

In a preferred aspect, the step of removing undifferentiated cells from mixed cells is conducted by capturing undifferentiated cells with a TRA-1-60 antibody, and removing the captured undifferentiated cells (TRA-1-60-positive cells) by an immune magnetic method (MACS).

The mixed cells obtained after the step of removing undifferentiated cells may be composed of only cardiomyocytes, endothelial cells, and mural cells, or may include optional cells besides cardiomyocytes, endothelial cells, and mural cells. The optional cells may include undifferentiated cells.

3. Layering of Cell Sheets

<Cell Sheet>

In the present invention, sheets of the aforementioned cells can be formed, for example, by culturing cells using cultureware coated with a temperature-responsive polymer, produced by polymerization of a (meth)acrylamide compound, an N- (or N,N-di)alkyl substituted (meth)acrylamide derivative (Japanese Unexamined Patent Application Publication No. 2010-255001), or a vinyl ether derivative, and changing the temperature, thereby removing sheets of cells. Examples of preferred cultureware include cultureware having poly-N-isopropylacrylamide inmmobilized thereon. This cultureware is commercially available as UpCell from CellSeed Inc. In addition, examples of temperature-responsive coating agents include cultureware coated with methylcellulose described in Chen C H, et al., Biomacromolecules, 7:736-43, 2006 or cultureware having a poly (ethyleneterephthalate (PET) film coated with a block copolymer composed of 2-ethoxyethylvinylether and 2-phenoxyethylvinylether described in Takamoto Y, et al., J. Biomater. Sci. Polymer Edn, 18:1211-1222, 2007. Upon producing cell sheets, these cultureware can be used as appropriate.

<Cardiac Cell Sheets>

In the present invention, cell sheets containing cardiomyocytes are preferably "cardiac cell sheets" made of mixed cells including cardiomyocytes, endothelial cells, and mural cells. Cell sheets mainly containing cardiomyocytes (for example, more than 80% per total cell number) are referred to as "cardiomyocyte sheets" for convenience to be distinguished from "cardiac cell sheet" described above. A method for producing such cardiac cell sheets from pluripotent stem cells may be carried out by producing cardiomyocytes, endothelial cells, and mural cells individually and mixing them after the production as the method described in WO 2012/133945, or by combining the methods of inducing their differentiation to induce the 3 types of cells simultaneously as the method (2. above) described in PCT/JP2013/058460.

As used herein, a cardiomyocyte refers to a cell expressing cardiac troponin (cTnT) or αMHC. An example of human cTnT is NCBI accession number NM_000364 and an example of mouse cTnT is NM_001130174. An example of human αMHC is NCBI accession number NM_002471 and an example of mouse αMHC is NM_001164171.

As used herein, an endothelial cell refers to a cell expressing one of PE-CAM, VE-cadherin, and the von Willebrand factor (vWF). A mural cell refers to a cell expressing smooth muscle actin (SMA). An example of human PE-CAM is NCBI accession number NM_000442 and an example of mouse PE-CAM is NM_001032378. An example of human VE-cadherin is NCBI accession number NM_001795 and an example of mouse VE-cadherin is NM_009868. An example of human vWF is NCBI accession number NM_000552 and an example of mouse vWF is NM_011708. An example of human SMA is NCBI accession number NM_001141945 and an example of mouse SMA is NM_007392.

<Layering of Cell Sheet>

In the present invention, cell sheets can be layered, by stacking cell sheets obtained in the method described above. A method for stacking cell sheets can be carried out by stacking cell sheets in any culture solution and removing the culture solution. During the stacking, the aforementioned hydrogel, for example, gelatin hydrogel, or preferably hydrogel particles, for example, gelatin hydrogel particles, dispersed in a phosphate buffer solution (PBS) or a culture solution are added (including, for example, application to a part or the entire surface) onto the surfaces of a cell sheet on which another cell sheet is overlaid. The hydrogel or preferably hydrogel particles may be dry or swollen in PBS or a culture solution. After addition of the hydrogel, for example, gelatin hydrogel, or preferably hydrogel particles, for example, gelatin hydrogel particles, they are preferably allowed to stand at 37° C. for 10 minutes or more, or preferably around 30 minutes. The hydrogel, for example, gelatin hydrogel, or preferably hydrogel particles, for example, gelatin hydrogel particles, to be used here may be dissolved in an isotonic solution at any concentration and used. Examples of the isotonic solution used here include physiological saline solutions and PBS. The amount of the hydrogel, for example, gelatin hydrogel, or preferably hydrogel particles, for example, gelatin hydrogel particles, added or applied is around 100 µg to 6000 µg, 200 µg to 5000 82 g, 300 µg to 4000 µg, 400 µg to 3000 µg or 500 µg to 2000 µg per unit area ($cm^2$) of cell sheet, and preferably an amount of 500 µg/$cm^2$ to 2000 µg/$cm^2$ per unit area ($cm^2$) of cell sheet.

In the present invention, the layered cell sheets may be produced by stacking a plurality of layered cell sheets, or may be produced by stacking a single layer of cell sheet and layered cell sheets. When stacking, the aforementioned hydrogel, preferably hydrogel particles, or more preferably gelatin hydrogel particles are added between the cell sheets. Alternatively, in the present invention, the aforementioned hydrogel, preferably the hydrogel particles, or more preferably the gelatin hydrogel particles are added between the first cell sheet or first layered cell sheets and the second cell sheet or second layered cell sheets. These layered cell sheets may be 2 or 3 cell sheets. As mentioned in the Background Art above, in layered cell sheets having 4 or more layers with no hydrogel being incorporated, the number of cells engrafted is usually not increased and also cell death occurs because the supply of oxygen, nutrients, etc. to cells is difficult. In contrast, the layered cell sheets according to the present invention have an advantageous characteristic of having increased cell number and thickness of layered cell sheets even in 4 or more layers of cell sheets.

The amount of the aforementioned hydrogel, preferably the hydrogel particles, or more preferably the gelatin hydrogel particles to be added between cell sheets is an amount that allows the hydrogel or hydrogel particles to spread over a part (for example, 10-30% or more or preferably 40-70% or more of the entire surface) or the entire surface of the face of the cell sheet and, for example, the exemplar amounts per unit area of the cell sheet are as described above.

The number of sheets in layered cell sheets may vary as appropriate depending on the purpose of use and examples include 4 or more, 5 or more, 6 or more, 7 or more, 8 or more, 9 or more, 10 or more, 15 or more, or 20 or more. For cardiomyocyte sheets or cardiac cell sheets, the thickness of sheets after layering is preferably around 500 μm or more, 600 μm or more, 700 μm or more, 800 μm or more, 900 μm or more, or 1 mm or more.

4. Pharmaceutical Composition Comprising Layered Cell Sheets

In the present invention, the layered cell sheets obtained in the method described above can be used for treatment by applying them directly to a portion damaged by disease or disorder. Therefore, the present invention provides pharmaceutical compositions comprising layered cell sheets. The layered cell sheets can be used in any cell number or any size or number of sheets depending on the species of animal with disease, the size of portion to be treated for disease, the therapeutic method of disease, etc.

The disease to be treated is chosen as appropriate depending on the cell type, but examples include therapeutic agents for corneal epithelial disease using corneal epithelial cell sheets or oral mucosa epithelial cell sheets; therapeutic agents for heart failure, chronic heart failure, severe heart failure, ischemic heart disease, myocardial infarction, acute myocardial infarction, chronic myocardial infarction, cardiomyopathy, ischemic cardiomyopathy, myocarditis, hypertrophic cardiomyopathy, dilated phase of hypertrophic cardiomyopathy, and dilated cardiomyopathy using cardiomyocyte sheets or cardiac cell sheets; therapeutic agents for reconstruction of esophagus epithelium, suppression of inflammatory reaction, and prevention of esophagostenosis using esophagus epithelial cell sheets or oral mucosa epithelial cell sheets; therapeutic agents for regeneration of periodontal tissue using periodontal ligamen cell sheets or dental pulp stem cell sheets; and therapeutic agents for degenerative arthritis using cartilage sheets including chondrocytes.

Although the present invention will be described more concretely with reference to the following examples, the scope of the present invention is not intended to be limited by these examples. Accordingly, although layered cardiac cell sheets are described as a specific example in the following examples, it should be noted that this is only an example and layered cell sheets of other types of cells can be also produced and good engraftment of cells to the living body is enabled according to the present invention.

EXAMPLES

Example 1

Generation of Layered Cardiac Cell Sheets
<Mouse ES Cell Line>

A mouse ES cell line (EMG7) engineered to express EGFP under control of aMHC promoter described in Yamashita J K, FASEB J. 19:1534-6, 2005, and an ES cell line (TFP-ROSA) modified to express TFP constitutively by a method described in Zambrowicz B P, Proc Natl Acad Sci USA, 94:3789-3794, 1997, were used.
<Flk+ Cell>

Flk+ cells were produced by a method previously reported (Yamashita J, et al. Nature, 408:92-6, 2000 or Yamashita J K, et al. FASEB J. 19:1534-6, 2005). Briefly, EMG7 or TFP-ROSA was cultured in a differentiation medium (αMEN supplemented with 10% fetal bovine serum and $5 \times 10^5$ mol/L 2-mercaptoethanol) on a gelatin-coated dish for 4 days and then Flk-positive cells were purified by FACS.
<Mixture of Endothelial and Mural Cells>

From Flk+ cells derived from TFP-ROSA obtained by the method described above, mixtures of endothelial and mural cells were produced by using a method previously reported (Yamashita J, et al. Nature, 408:92-6, 2000 or Yurugi-Kobayashi T, et al. Arterioscler ThrombVasc Biol. 26:1977-84, 2006). Briefly, the mixtures were obtained by culturing the cells on a gelatin-coated dish for 3 days using the differentiation medium supplemented with 50 ng/ml VEGF and 0.5 mmol/L 8-bromo-cAMP.
<Cardiomyocyte>

From Flk+ cells derived from EMG7 obtained by the method described above, cardiomyocytes were produced by using a method previously reported (WO 2009/118928 or Yan P, et al. Biochem Biophys Res Commun. 379:115-20, 2009). Briefly, cardiomyocytes were obtained by culturing the Flk+ cells on OP9 cells treated with mitomycin C in the differentiation medium supplemented with 1-3 μg/mL Cyclosporin-A for 4 days and then isolating the GFP-positive fraction.
<Cardiac Cell Sheet>

Figure 1:
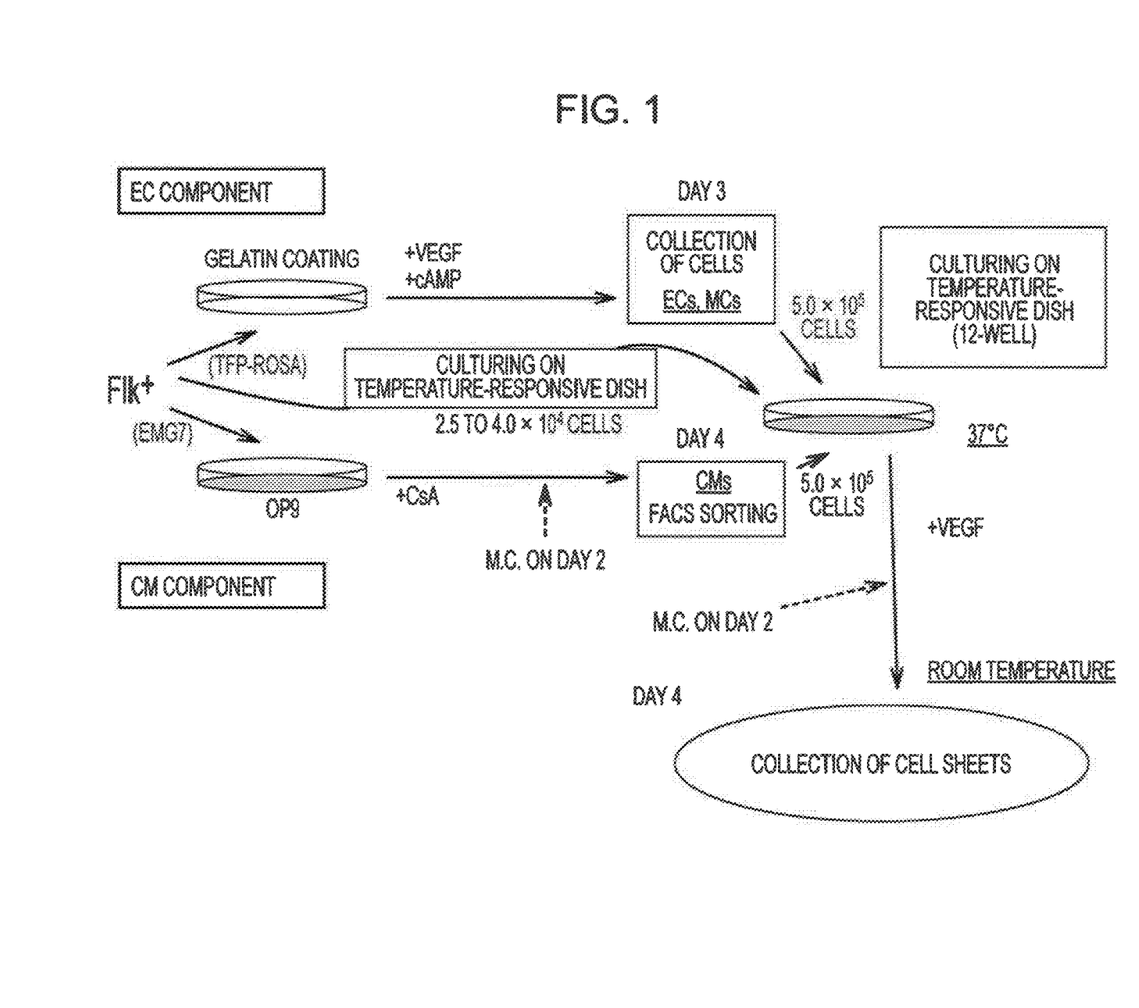
FIG. 1 illustrates a protocol for the formation of cardiac cell sheets. In the figure, EC stands for endothelial cell, VEGF for vascular endothelial growth factor, cAMP for cyclic AMP, MC for mural cell, CM for cardiomyocyte, CsA for cyclosporine A, and M.C. for medium change.

Using the aforementioned Flk+ cells, mixtures of endothelial and mural cells, and cardiomyocytes, cardiac cell sheets were produced by a method described in Masumoto H, et al., Stem Cells, 301196-205, 2012, as illustrated in FIG. 1. Briefly, $2.5 \times 10^4$ to $4.0 \times 10^4$ Flk+ cells derived from TFP-ROSA were plated on a 12-well thermosensitive culture dish (UpCell, CellSeed Inc.), and on day 4 of culturing, $5.0 \times 10^5$ cells of the aforementioned mixture of endothelial and mural cells and $5.0 \times 10^5$ cells of the aforementioned cardiomyocytes were plated onto the same culture dish. These cells were cultured in the differentiation medium supplemented with VEGF at 37° C. Four days after adding cardiomyocytes (on day 7 of culturing), cells were removed as a sheet from the culture dish by returning the temperature to room temperature to obtain a cardiac cell sheet. A medium change was carried out 2 days after mixing the 2 kinds of cells.

<Gelatin Hydrogel Particle>

600 ml of olive oil (Wako Pure Chemical Industries, Ltd.) was added to a 1 L three neck flask and heated in a water bath at 40° C. with stirring by a propeller for 1 hour. Then, 20 ml of 10 wt % aqueous solution of gelatin (derived from bovine bone, isoelectric point: 5.0; weight average molecular weight: $1.0 \times 10^5$, provided from Nitta Gelatin Inc.) preheated to 40° C. was added to the flask and stirred at a rotational speed of 400 rpm for 10 minutes to form a W/O emulsion. This emulsion was cooled to 0° C. and stirred at a rotational speed of 400 rpm for 1 hour to make gel from the gelatin aqueous solution. Subsequently, the gelatin was dehydrated by adding 200 ml of cold acetone and stirring at a rotational speed of 200 rpm for 15 minutes. The solution in the flask was then collected into a 50 ml Falcon tube and centrifuged at a rotational speed of 5000 rpm at 4° C. for 5 minutes. After removing the supernatant, the precipitate was washed with cold acetone and stirred by a homogenizer (at a rotational speed of 10000 rpm) for 1 minute. Subsequently, the resultant suspension was centrifuged at 4'C at a rotational speed of 5000 rpm for 5 minutes. The supernatant was removed again, the precipitate was washed, and the suspension was centrifuged, and then these operations were repeated 3 times. While being washed with cold acetone, gelatin particles were fractioned with sieves (20, 32, and 53 μm openings), collected separately according to particle diameters, and vacuum-dried to obtain dry particles. Then, uncross-linked gelatin particles were chemically cross-linked by thermal dehydration of the gelatin particles for 48 hours at 140° C. under a reduced pressure in a vacuum oven to obtain gelatin hydrogel particles. Those having particulate diameters of less than 20 μm, 20-32 μm, and 32-53 μm were used.

<Layering of Cardiac Cell Sheets>

Figure 2:
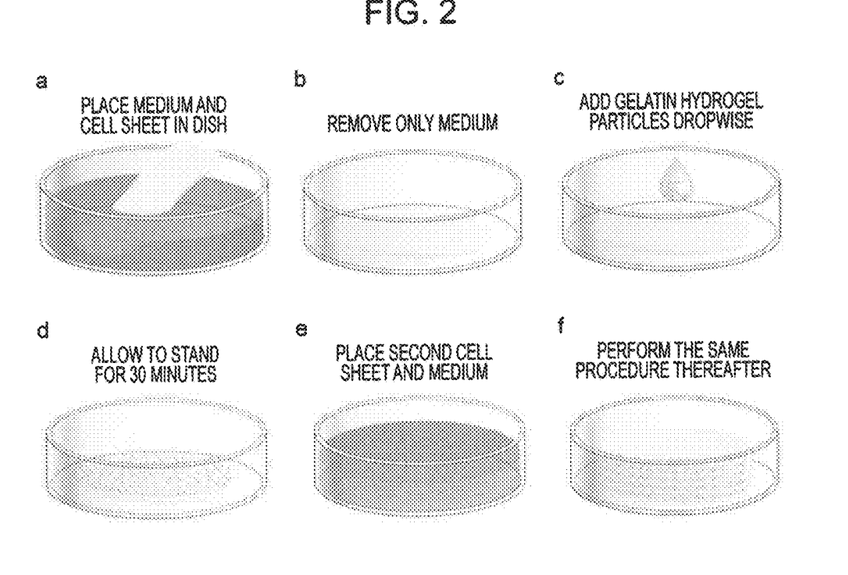
FIG. 2 illustrates the steps for layering cell sheets using gelatin hydrogel fine particles by the method according to the present invention. Panel a illustrates the step of placing and leaving a sheet flat on a gelatin-coated culture dish; Panel b illustrates the step of aspirating the medium and settling the culture dish and the sheet; Panel c illustrates the step of adding gelatin hydrogel fine particles dropwise on the cell sheet. Panel d illustrates the step of incubating at 37° C. for 30 minutes. Panel e illustrates the step of layering another cell sheet after the gelatin hydrogel treatment. Panel f is an illustration of cell sheets after repeating the layering for 5 layers.

The method described above was used, but the half amounts of cells were used for all cells. A cardiac cell sheet produced in a 24-well plate was placed and left flat on a gelatin-coated culture dish. The medium was then aspirated to settle the culture dish and the sheet. The cardiac cell sheet was about 6 mm in diameter. 2.5 μl (about 885 μg/cm$^2$; low dose) or 7.5 μl (about 2654 μg/cm$^2$; high dose) of gelatin hydrogel particles having particulate diameters of 20 to 32 μm in a dry state dispersed at a concentration of 0.1 mg/μl in a PBS solution were added thereon dropwise and incubated at 37° C. for 30 minutes. Subsequently, another cardiac cell sheet was added with the differentiation medium and layered on the cardiac cell sheet treated with the gelatin hydrogel particles. The medium was then removed. The same operations were repeated to get 5 cardiac cell sheets layered (FIG. 2). When layering, the second, third, fourth, and fifth layers were placed at the positions slightly shifted from those of the first, second, third, and fourth layers, respectively. Finally, the differentiation medium was added in such a way that the medium ran along the bottom face of the culture dish using Pipetman to detach the layered cardiac cell sheets from the culture dish.

The layered cardiac cell sheets obtained were compared with a control group and it was found that the sheets in the gelatin hydrogel particle group continued self-beating longer than those in other groups. As the control in the comparison, cardiac cell sheets layered without adding gelatin hydrogel particles were used.

Figure 3:
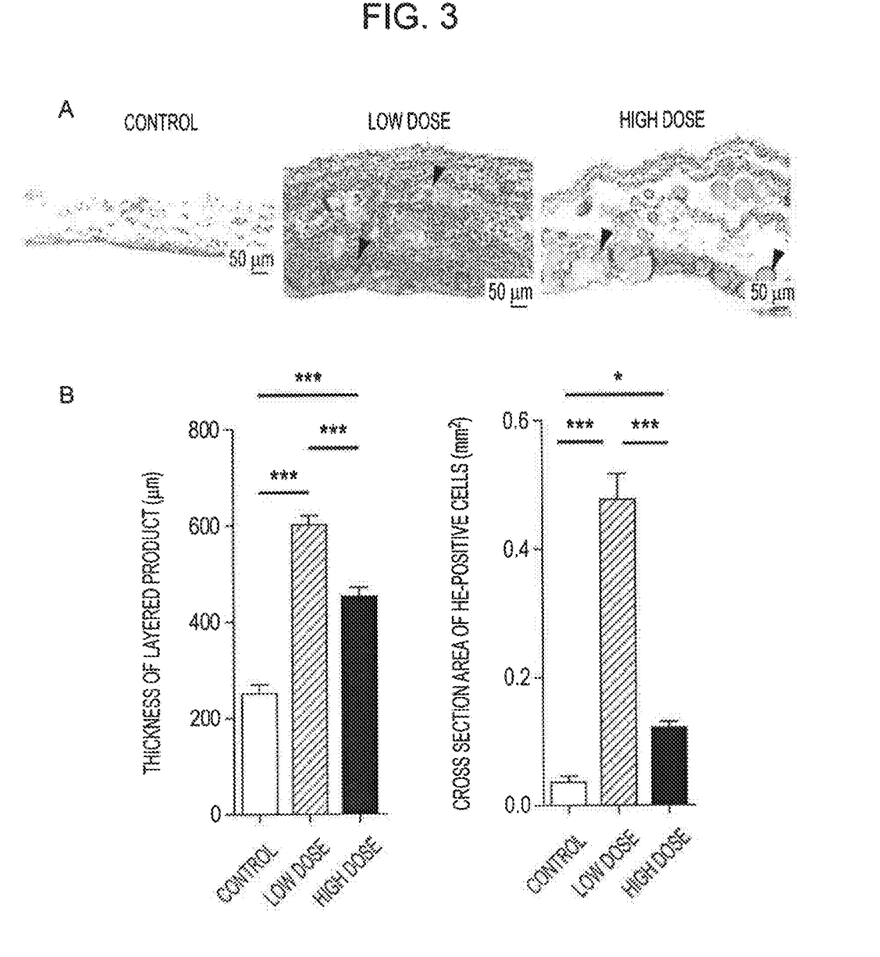

In order to examine the obtained layered cardiomyocyte sheets with staining, the sheets were fixed with 4% PFA, dehydrated, defatted, dealcoholized, and then infiltrated with paraffin, and then embedded in paraffin. The paraffin embedded sample was sliced into 6 μm sections and stained with hematoxylin eosin (HE) (FIG. 3A). As a result, the thickness and the living cell region area of the layered sheets were significantly greater in the low dose group compared with those in the control group and the high dose group (FIG. 2B). (Thickness, ctrl (control group): 250.9±17.7 μm, n=7 vs. low dose group: 597.1±24.0 μm, n=10 vs. high dose group: 449.2±25.6 μm, n=5, p<0.0001, HE staining-positive cell region area; ctrl (control group): 0.03511±0.009244 mm$^2$, n=5, low dose group: 0.4746±0.04162 mm$^2$, n=3 vs. high dose group: 0.1211±0.007000 mm$^2$, n=4, p=0.0090.)

It was also possible to obtain layered cardiac cell sheets with 5 layers (about 1 cm in diameter) produced using 12-well plates similarly by adding dropwise 5 μl (about 637 g/cm$^2$) or 15 μl (about 1911 μg/cm$^2$) of gelatin hydrogel particles having particulate diameters of 20-32 μm in a dry state suspended at a concentration of 0.1 mg/μl in a PBS solution.

Furthermore, it was confirmed that 15 layers of layered cardiac cell sheets (with a thickness about 1 mm) can be obtained by a similar process.

<Examination of Effect of Particle Diameter of Gelatin Hydrogel Particles>

Figure 4:
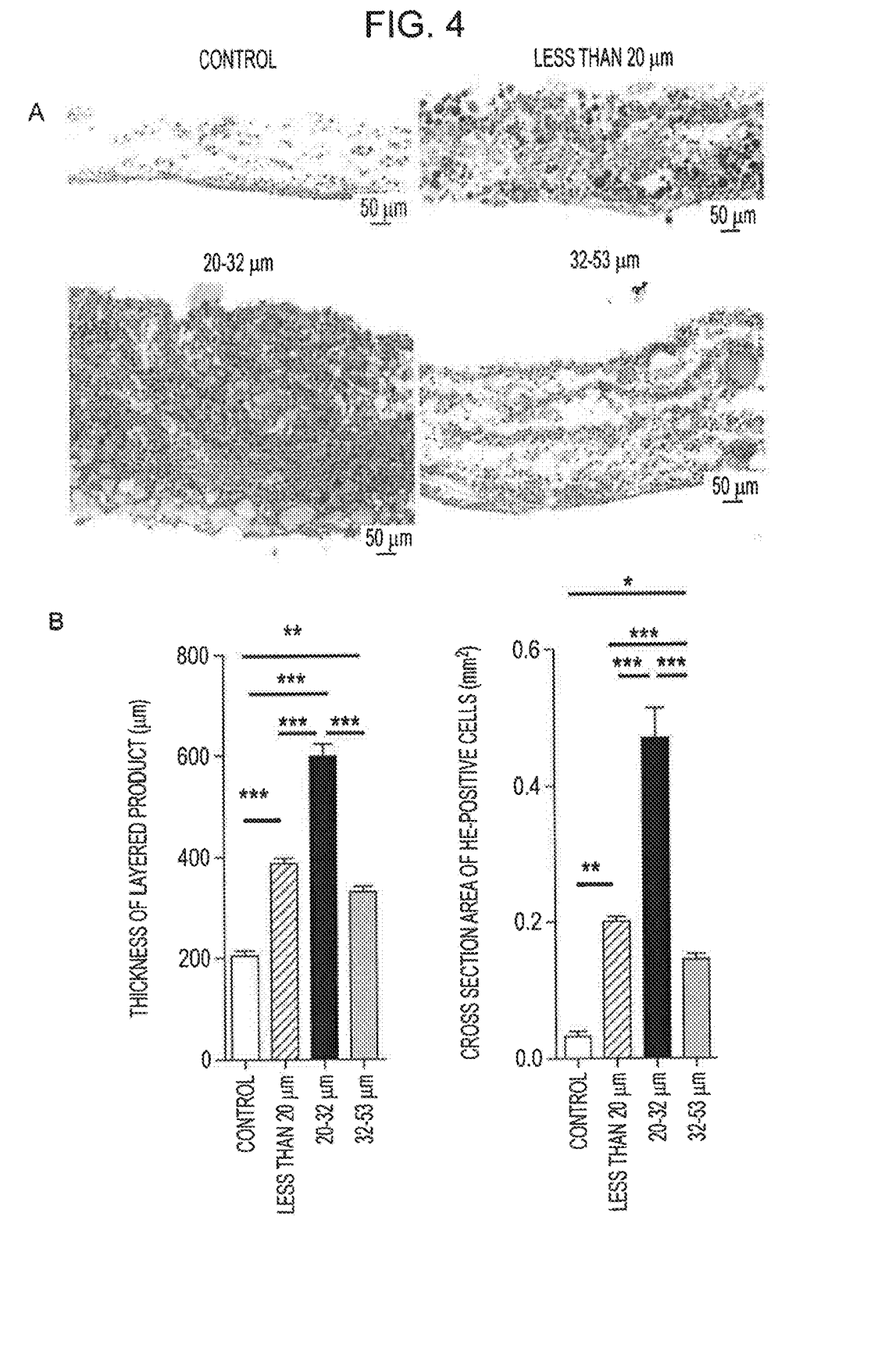

In the aforementioned layering of cardiac cell sheets, gelatin hydrogel particles having particulate diameters of less than 20 μm, 20-32 μm, and 32-53 μm in a dry state were used to layer cardiac cell sheets. The thickness and the living cell region area of the layered sheets were the greatest in the 20-32 μm group among the 4 groups of ctrl (control), less than 20 μm, 20-32 μm, and 32-53 μm groups (FIGS. 4 A and B). (Thickness, ctrl: 204.7±9.5 μm, n=5 vs. less than 20 μm group: 389.1±7.6 μm, n=3 vs. 20-32 μm group: 597.1±24.0 μm, n=10 vs. 32-53 μm group: 333.5±5.7 μm, n=3, p<0.0001, HE staining-positive cell region area; ctrl: 0.03446±0.005362 mm$^2$, n=3 vs. less than 20 μm group: 0.2051±0.004676 mm$^2$, n=3 vs. 20-32 μm group: 0.4746±0.04162 mm$^2$, n=3 vs. 32-53 μm group: 0.1487±0.003894 mm$^2$, n=3, p <0.0001).

Example 2

Transplantation Test of Layered Cardiac Cell Sheets into Myocardial Infarction Model Rat Layered cardiac cell sheets (5 layers) produced in Example 1 were transplanted by the method of Masumoto et al., (Masumoto H, et al., Stem Cell 30:1196-1205 (2012)) on the surface of anterior wall of the heart in myocardial infarction model rats prepared from athymia nude rats (male, 10-12 weeks of age) by a known technique (Masumoto H, et al., the same as above, Stem Cell 30:1196-1205 (2012), Nishina T, et al., Circulation 104:I241-I245 (2001), Sakakibara Y., et al., Circulation 106: I913-I197 (2002)). Echocardiography was performed before the ligation (baseline), on the 6th day (pre TX), 1 week, 2 weeks, 4 weeks, 8 weeks, and 12 weeks after myocardial infarction. The left ventricular diastolic diameter (LVDd) and shrinkage period diameter (LVDs) and the left ventricular diastolic wall thickness (LVWTd) and the shrinkage period wall thickness (LVWTs) of infarction and non-infarction walls were measured and the change of the left ventricle (LV) shortening rate (FS (%)) over time was calculated from the following formula:

$$FS\ (\%) = (LVDd - LVDs)/LVDd$$

Figure 5:
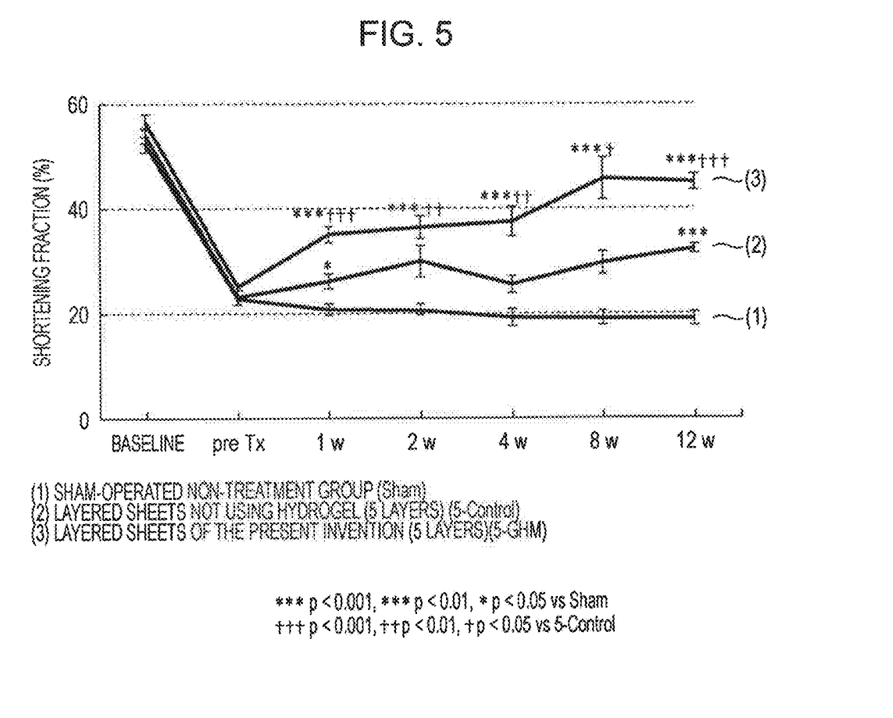
FIG. 5 is a graph illustrating the change of the left ventricle (LV) shortening rate (%) over time upon the transplantation of layered seats (5 layers) of the present invention onto the cardiac anterior wall of myocardial infarction model rats generated from athymia nude rats (male, 10-12 week old) by a known method. In the figure, (1) represents the sham-operated non-treatment group, (2) represents layered sheets not using gelatin hydrogel (5 layers), and (3) represents layered sheets of the present invention (5 layers).

The result is shown in FIG. 5. The figure shows that the group having the cardiac cell sheets layered using gelatin hydrogel particles has improved cardiac functions with statistically significant differences from the untreated group as well as the group having the cardiac cell sheets layered without using gelatin hydrogel particles.

INDUSTRIAL APPLICABILITY

In the production of layered cell sheets according to the present invention, cell sheets can be layered with cells alive. Therefore, the resultant cell sheets can be used for the application to cell replacement therapies.

All the publications, patents, and patent applications cited herein are incorporated herein by reference in their entirety.

The invention claimed is:

1. A layered cell sheet product comprising cell sheets layered using hydrogel particles, wherein
the hydrogel particles are present between the cell sheets,
the hydrogel particles have particulate diameters of 20 to 32 μm in a dry state, wherein the hydrogel particles are present between the cell sheets in an amount of 100 to 6000 μg/cm² unit area, and
wherein the hydrogel particles are a material selected from the group consisting of water-soluble polymers, hydrophilic polymers, water absorptive synthetic polymers, polysaccharides, and proteins.

2. The layered cell sheet product according to claim 1, wherein the hydrogel particles are gelatin hydrogel particles.

3. The layered cell sheet product according to claim 2, wherein the gelatin hydrogel gel particles are gelatin hydrogel particles having intermolecular cross-linking between gelatin molecules.

4. The layered cell sheet product according to claim 1, wherein the hydrogel particles are present between the cell sheets at an amount of 500 to 2000 μg/cm² unit area.

5. The layered cell sheet product according to claim 1, wherein the total number of the cell sheets is 4 to 20.

6. The layered cell sheet product according to claim 1, wherein the cell sheets comprise cardiomyocytes.

7. The layered cell sheet product according to claim 1, wherein the cell sheets are cardiac cell sheets comprising cardiomyocytes, endothelial cells, and mural cells.

8. The layered cell sheet product according to claim 7, wherein cardiomyocytes, endothelial cells, and mural cells are produced from induced pluripotent stem cells.

9. A pharmaceutical composition comprising the layered cell sheet product according to claim 1.

10. The pharmaceutical composition according to claim 9, wherein the pharmaceutical composition is for use in treatment of heart diseases.

11. A method for producing the layered cell sheet product according to claim 1, comprising the steps of:
(1) preparing a plurality of cell sheets;
(2) placing hydrogel particles on one of the cell sheets and then layering thereon another one of the cell sheets;
(3) repeating the step (2); and
(4) yielding a layered product having a predetermined number of the above cell sheets;
wherein the hydrogel particles have particulate diameters of 20 to 32 μm in a dry state.

12. The method according to claim 11, wherein the hydrogel particles are placed between the cell sheets at an amount of 500 to 2000 μg/cm² unit area.

13. The layered cell sheet product according to claim 1, wherein the hydrogel particles are placed between the cell sheets at an amount of 300 to 4000 μg/cm² unit area.

14. The layered cell sheet product according to claim 1, wherein the hydrogel particles are collagen or a collagen hydrolysate.

15. The layered cell sheet product according to claim 1, wherein the hydrogel particles are polyacrylamide hydrogel particles.

16. The layered cell sheet product according to claim 1, wherein the hydrogel particles are polysaccharide hydrogel particles.

* * * * *